United States Patent [19]

Klingler et al.

[11] Patent Number: 5,527,923

[45] Date of Patent: Jun. 18, 1996

[54] PROCESS FOR PREPARING ENANTIOMERICALLY PURE DIARYLPROLINOLS

[75] Inventors: Franz D. Klingler, Griesheim; Rainer Sobotta, Ingelheim, both of Germany

[73] Assignee: Boehringer Ingelheim KG, Ingelheim am Rhein, Germany

[21] Appl. No.: 434,225

[22] Filed: May 4, 1995

[30] Foreign Application Priority Data

May 13, 1994 [DE] Germany .................... 44 16 963.9

[51] Int. Cl.⁶ .................................................. C07D 207/08
[52] U.S. Cl. ............................................................ 548/570
[58] Field of Search ............................................. 548/570

[56] References Cited

U.S. PATENT DOCUMENTS 5,039,802  8/1991  Blacklock et al. ..................... 546/165

OTHER PUBLICATIONS

"The First Enantioselective Total Syntheses of the Allopumiliotoxin A Alkaloids 267A and 339B", Goldstein et al., J. Org. Chem., 1992, vol. 57, pp. 1179–1190.

"Highly Enantioselective Borane Reduction of Ketones Catalyzed by Chiral Oxazaborolidines, Mechanism and Synthetic Implications" –E. J. Corey et al., J. Am. Chem. Soc., 1987, vol. 109, pp. 5551–5553.

"Synthesis of (S)–(–)alpha, alpha–Diphenyl–2–pyrrolidinemethanol", Y. Liao–Chemical Abstracts, vol. 119, No. 11, 13–Sep. 1993; C.A.: 117057j.

"Convenient Method for the Synthesis of Chiral α,α–Diphenyl–2–pyrrolidinylmethanol"–J. V. Bhaskar Kanth et al., Tetrahedron, vol. 49, No. 23, 1993, pp. 5127–5132.

"A Practical Enantioselective Synthesis of α,α–Diaryl–2–pyrrolidinemethanol. Preparation and Chemistry of the Corresponding Oxazaborolidines"–D. J. Mathre et al., J. Org. Chem., 1991, vol. 56, pp. 751–762.

"Large Scale Preparation of Versatile Chiral Auxiliaries Derived from (S)–Proline" –D. Enders et al., Bull. Soc. Chim. Belg., vol. 97, No. 8–9, 1988, pp. 691–704.

Primary Examiner—Joseph Paul Brust
Attorney, Agent, or Firm—R. P. Raymond; M-E. M. Devlin; A. R. Stempel

[57] ABSTRACT

The present invention relates to a new process for preparing enantiomerically pure diarylprolinols, especially (R)-(+)- or (S)-(–)-2-(diphenylhydroxymethyl)-pyrrolidine (R)-(+)- or (S)-(–)-α,α-diphenyl-(2-pyrrolidinyl)-methanol) starting from proline.

3 Claims, No Drawings

PROCESS FOR PREPARING ENANTIOMERICALLY PURE DIARYLPROLINOLS

The present invention relates to a process for preparing enantiomerically pure diarylprolinols, particularly (R)-(+)- or or (S)-(−)-2-(diphenylhydroxymethyl)-pyrrolidine ((R)-(+)- or (S)-(−)-α,α-diphenyl-(2-pyrrolidinyl)-methanol) starting from proline.

Diarylprolinols, especially diphenylprolinols, and specifically di-2-naphthylprolinol [Tetrahedron Lett 31, 601 (1999)], are used as chiral catalysts for the enantioselective reduction of prochiral ketones. They may be used in reductions on an industrial scale.

The actual reducing agents are the corresponding oxazaboralidines, which are obtained by reacting the diarylprolinols with suitable boranes.

The discovery of the possibility of using oxazaboralidines in the enantioselective reduction of prochiral ketones has led to considerable interest in this group of compounds. [G. J. Quallich and T. M. Woodall, Synlett. 1993, 929].

In the last two decades in particular, a number of methods of synthesising these compounds have been published. The main intermediate products are the diarylprolinols. Only the final step contains the reaction with the desired borane, as mentioned above.

Thus, for example, there are numerous different methods known for preparing (S)-1,1-diphenylprolinol. For example, French Patent 976 435 discloses a process in which the ethylester of 1-proline is reacted with phenyl magnesium bromide to form the corresponding α-pyrrolidinyldiphenyl-carbinol. The product yield obtainable by this process is, however, rather low.

In addition, D. Enders et al. describe a method of preparation in which pyrrolidine is first converted, into the corresponding N-nitrosamine with ethyl nitrite, which after deprotonation with diisopropylamide and reaction with benzophenone followed by reductive cleavage of the nitroso-protecting group, yields the desired 2-(diphenylhydroxymethyl)pyrrolidine in the form of a racemic mixture [D. Enders, R. Pieter, B. Renger and D. Seebach, Org. Syn. 58 (1978) 113]. Apart from the disadvantage that a racemic mixture is produced, N-nitrosopyrrolidine is an intermediate in this process, and it is known to cause tumours in animal trials.

Other processes are described, inter alia, by Corey et al. [J. Am. Chem. Soc. 109 (1987) 7926], Kapfhammer et al. [Hoppe-Seylers Zeit. Physiol. Chem. 223 (1933) 43] and in German Offenlegungsschrift 3 609 152.

In addition, E. J. Corey has described a multi-stage synthesis (J. Am. Chem. Soc. 109 (1987) 5551] in which (S)-1,1-diphenylprolinol is obtained in a total yield of 30–40%. However, this process requires the isolation of all the intermediate products, such as N-(benzyloxycarbonyl)-S-proline and N-(benzyloxycarbonyl)-S-proline methylester. In addition to using a relatively expensive protecting group, this process has the drawback that an excess (seven equivalents) of phenyl magnesium chloride is required in order to carry out the Grignard reaction Of the N-(benzyloxycarbonyl)-S-proline methylester. Furthermore, isolation of the diphenylprolinol, in the presence of the magnesium compounds which are produced in large quantities by the Grignard reaction, presents technical problems. The magnesium hydroxide gel has to be extracted several times in order to achieve this.

A simpler method of preparation is disclosed in European Patent Application EP-A-0 453 298. Starting from S-proline, first the (S)-tetrahydro[1H,3H]pyrrolo-[1,2-c]-oxazol-1,3-dione is prepared; in order to do this, S-proline first has to be reacted with phosgene and then reacted with the triethylamine in the subsequent reaction step [Fuller et al., Biopolymers 15, (1976) 1869] (cf. Example 1). The resulting carboxanhydride is reacted with the corresponding aryl magnesium halide (in this case, phenyl magnesium chloride) to obtain the desired (S)-α,α-diphenyl-2-pyrrolidine methanol, which is obtainable by this method in a yield of 73% of theory. However, the disadvantage of this process is that, owing to the use of phosgene, the reaction equipment is subjected to more stringent safety requirements.

From the point of view of economic and safe production on an industrial scale, the processes known from the prior art are unsuitable.

The aim of the present invention is therefore to overcome the disadvantages of the preparation methods known from the prior art.

According to the invention, this objective is achieved by the fact that, in the first reaction step with benzyl chloride, the pyrrolidine nitrogen in the proline is protected with the corresponding benzyl protecting group and at the same time the free carboxyl function is converted into the corresponding benzyl ester.

In the second reaction step, the corresponding Grignard product, in this case N-benzyl-2-(diphenylhydroxymethyl)-pyrrolidine, is obtained by reaction with an aryl magnesium halide, for example by reaction with phenyl magnesium chloride.

In the last reaction step, the benzyl protecting group is cleaved by catalytic hydrogenation.

Apart from the advantage that no dangerous materials are used in the reaction sequence the process of the invention has the further advantage that the reaction products obtained in the individual reaction steps do not need to be isolated or purified.

The individual steps of the process are carried out as follows:

In order to carry out the first reaction step, the desired quantity of D- or L-proline is placed in an inert solvent. Suitable reaction media for carrying out this protection include all solvents which are known from the prior art, especially for reactions of benzylation [cf. T. W. Greene, Protective Groups in Organic Synthesis, John Wiley & Sons, New York 1981]. Preferably, organic sulphoxides such as dimethylsulphoxide or acid amides, of which dimethylformamide is particularly preferred, are used. The protection of the carboxyl function and the amino function—for example with aralkyl halides—is preferably carried out in the presence of basic compounds, such as suitable alkali or alkaline earth metal compounds, of which alkali metal salts are preferred. It is particularly preferable to use sodium hydrogen carbonate. The protecting groups to be used for the desired protection are also known from the prior art [see T. W. Greene loc. Cit.]. For this purpose, aralkyl halides are preferably used, and the use of benzyl chloride is particularly preferred. The reactants are preferably reacted at elevated temperatures. Preferably, the reaction is carried out in a temperature range from 60° to 140° C., temperatures in the range from 80° to 100° C. being particularly preferred (it goes without saying that the choice of suitable reaction temperature depends on the nature or reactivity of the reactants used).

After the reaction has ended, the reaction mixture is preferably cooled to a temperature in the range from about 20° to 40° C. and water is added.

The reaction mixture thus obtained is then extracted with a suitable extracting agent. Hydrocarbons, particularly alkanes such as petroleum ether fractions, or aromatic hydrocarbons are suitable for this purpose, whilst toluene is particularly preferred as an extracting agent.

After the combined extracts have been evaporated down, preferably under mild temperatures and appropriately in the range from about 30°–100° C., under reduced pressure, the distillation residue remaining is used in the second step of the reaction without any further purification.

Within the course of the following step of the synthesis, the previously protected proline derivative (or when benzyl halides are used as the protecting agent, the corresponding dibenzyl proline) is reacted with a correspondingly selected Grignard compound to obtain the desired prolinol derivative. The corresponding reactions and suitable Grignard compounds are known per se from the prior art. [J. March, Advanced Organic Chemistry, 3rd Edition, p. 434, John Wiley and Sons, New York, 1985 and cited literature].

Preferably, aryl magnesium halides are used as Grignard compounds. Thus, for example, it is particularly preferred to use phenyl magnesium chloride in order to prepare diphenyl prolinol. β-naphthyl magnesium halides may also be used as Grignard compounds.

In order to carry out the Grignard reaction, the proline derivative protected in the first step, for example, is reacted in solution with the Grignard reagent. The solvent may be any solvent which is inert under the reaction conditions and which does not have a detrimental effect on the course of the reaction. The solvents which might be used for this are known from the prior art. It is preferable to use ethers, of which cyclic ethers such as tetrahydrofuran are particularly preferred. The reaction is carried out at elevated temperature, depending on the reactivity of the educts. A reaction temperature in the range from 50° to 90° C. is preferred, and a reaction temperature of about 70° C. is particularly preferred. Moreover, the reaction is preferably carried out under an inert gas atmosphere.

After the reaction has ended, the reaction mixture is cooled to ambient temperature, i.e. a temperature in the range from 15° to 35° C., and the products are hydrolysed. Hydrolysis is preferably carried out with an aqueous solution of an acid, the dilute aqueous solution of an inorganic acid such as sulphuric acid being particularly preferred. Depending on the exothermic nature of the hydrolysis reaction, it may be necessary to cool the reaction mixture during hydrolysis.

Once hydrolysis is complete, the pH is adjusted, if necessary, to the neutral range, preferably 7, by the addition of more acid. The aqueous phase is stirred once more with an organic solvent, preferably the ether originally used and most preferably tetrahydrofuran.

The organic phase is optionally evaporated down in a water jet vacuum at elevated temperature, preferably in the range from 50° to 60° C., and the residue is isolated without any further purification.

In the last step, the protecting group is cleaved from the amino function. The methods of removing the protecting groups are also known per se from the prior art. Thus, for example, a benzyl protecting group can easily be cleaved under reductive conditions. In order to do this, the corresponding N-benzyl prolinol derivative is dissolved in a suitable solvent, preferably an alcohol and particularly preferably ethanol, and reacted in the presence of a catalyst (preferably palladium on charcoal, a catalyst with a palladium content of 10% being particularly preferred) with hydrogen under elevated pressure, preferably in a pressure range from 2 to 20 bar, more preferably 3 to 7 bar. After the hydrogenlysis of the N-benzyl bond has been completed, the catalyst is filtered off and the filtrate is evaporated down under reduced pressure, preferably in a water jet vacuum, and, depending on the reaction medium used, at elevated temperature up to 70° C. In order to purify or isolate the prolinol derivative thus prepared, the residue remaining is dissolved in a suitable solvent, preferably in an aliphatic or aromatic hydrocarbon, most preferably in toluene, then filtered. The filtrate is mixed with the aqueous solution of an acid, preferably an inorganic acid, most preferably 15% Sulphuric acid. The aqueous solution is adjusted to a pH below 7 and preferably to a pH in the range from 1 to 4 and most preferably a pH in the range from 2 to 3, whereupon the corresponding salt of the α,α-diarylprolinol is precipitated after vigorous stirring. The resulting suspension is suction filtered and the filter cake is then washed.

In order to liberate the free base, the salt of the diarylprolinol derivative, possibly still wet from the filtration, is suspended in an inert solvent, preferably in a halogenated hydrocarbon and most preferably in dichloromethane, with vigorous stirring. The suspension is then mixed—until separation occurs—with water and then with a solution of a base, preferably with a dilute aqueous solution of an alkali or alkaline earth metal compound and most preferably with 25% aqueous sodium hydroxide solution, until a pH above 7, preferably in the range from 8 to 12 and most preferably 9, is obtained. After intensive mixing of the organic and aqueous solution and subsequent phase separation plus exhaustive extraction of the aqueous phase, the combined organic extracts are evaporated down, preferably under reduced pressure and most preferably in a water jet vacuum, and the desired prolinol derivative is isolated.

The following Examples are non-limiting illustrations of the invention.

EXAMPLE 1

(Benzylation):

230 g (2 mol) of L-proline are placed in 2.4 liters of dimethylformamide in a 6 liter flask and 420 g (5 mol) of sodium hydrogen carbonate and 633 g (5 mol) of benzyl chloride are added thereto. The reaction mixture is then stirred at a temperature of 100° C. for a period of about 4 hours. Then the resulting suspension is cooled to ambient temperature and added, with stirring, to 8.7 liters of water. The aqueous solution is extracted three times with toluene and the combined extracts (about 1.3 liters) are distilled off in vacuo at 40 to 50 Torr.

At a temperature of about 80° C. and under a pressure of 25–30 Torr, dimethylformamide and unreacted benzyl chloride are separated off by distillation, leaving 667 g of distillation residue in the form of a brown oil. Further distillation over a period of 3 hours at a temperature in the range from 80°–120° C. under a pressure of 2 to 10 Torr yields 639 g of a brown oil (N-benzyl-L-proline benzyl ester).

EXAMPLE 2

(Grignard reaction):

657.5 ml (1.25 mol) of a 25% by weight solution of phenyl magnesium chloride are placed in a 4.5 liter flask flushed with an inert gas and heated to reflux temperature. Over a period of 30 minutes a solution of 147.7 g (0.5 mol) of N-benzyl-L-proline benzyl ester in 500 ml of tetrahydrofuran is added dropwise with stirring. Then the reaction mixture is heated to reflux temperature once more, unpil virtually no N-benzyl-L-proline benzyl ester can be detected by thin layer chromatography. The mixture is then cooled to ambient temperature and is mixed with 1500 ml of dilute sulphuric acid (300 ml of 15% by weight sulphuric acid+ 1200 ml of water) at a temperature in the range from 10° to 20° C. with vigorous stirring. The hydrolysis mixture is then neutralised (pH=7) with a further 26 ml of 15 weight-% sulphuric acid. The aqueous phase is stirred with tetrahydrofuran. After phase separation and extraction, the combined organic extracts are concentrated down under a Water jet vacuum at 55° C., leaving 221.6 g of the N-benzyl-α,α-diphenylprolinol as distillation residue.

EXAMPLE 3

(Debenzylation):

110.25 g of the N-benzyl-α,α-diphenylprolinol prepared in step 2 are dissolved in 1700 ml of ethanol and hydrogenated in the presence of 18 g of catalyst (10% palladium on charcoal) at 70° C. under a hydrogen pressure of 5 bar for a period of about 5.5 hours. Then the catalyst is filtered off. The filtrate is evaporated down under a water jet vacuum at a temperature of about 60° C. leaving α,α-diphenyl-L-prolinol as distillation residue (about 167 g).

EXAMPLE 4

(Purification):

The distillation residue obtained in Example 3 is dissolved in 2.5 liters of warm toluene and the resulting cloudy solution is filtered through a Seitz filter (0=10 cm) Supra 500. The filter residue is washed with 500 ml of toluene and the filtrate is diluted with a further 500 ml of toluene. 142 ml of 15% by weight sulphuric acid are added with vigorous stirring, whereupon a pH in the range from 2–3 is obtained in the emulsion and the sulphate of the α,α-diphenyl-L-prolinol is precipitated. The resulting viscous suspension is stirred for about another hour and left to stand for a period of about 12 hours at ambient temperature to crystallise out. Then the suspension is suction filtered and the filter cake is washed with 700 ml of toluene. The sulphate, still wet from filtering, is then suspended in 3 liters of dichloromethane, with vigorous stirring. The suspension is combined with 1 liter of water and with 53 ml of 25% sodium hydroxide solution, resulting in a pH of about 9. After 1 hour's stirring, the phases are separated and the aqueous phase is extracted again with 500 and 300 ml of dichloromethane. The combined organic extracts are evaporated down in a water jet vacuum and dried at 50° C. in vacuo, leaving 96.6 g (76.2% of theory) of the diphenyl-L-prolinol in the form of brown crystals.

What is claimed is:

1. Process for preparing enantiomerically pure dibenzyl prolinols, characterized in that
   a) D- or L-proline is dissolved in an inert solvent and reacted with benzyl halide, at a temperature in the range from 60° to 140° C. and, after cooling, combined with water, then the reaction mixture is extracted with a hydrocarbon and the dibenzyl, protected D- or L-proline derivative is isolated and
   b) the dibenzyl protected D- or L-proline derivative is dissolved in an inert solvent and reacted with an aryl Grignard compound at a temperature in the range from 50° to 90° C. and, after the reaction mixture has cooled, it is combined with a dilute solution of an inorganic acid, and adjusted to a pH in the neutral range and the aqueous phase is extracted with an organic extraction agent, and the dibenzyl prolinol derivative is isolated and
   c) the dibenzyl prolinol derivative is dissolved in an alcohol and, in the presence of a substance which catalyses; the reductive cleaving of the benzyl protecting group it is reacted with hydrogen under elevated pressure in the range from 2 to 20 bar, and the prolinol derivative freed from the benzyl protecting group, and after removal of the reaction medium, is dissolved in an aliphatic or aromatic hydrocarbon, the solution is filtered and the filtrate is combined with an aqueous solution of an inorganic acid, until a pH of less than 7 is achieved, the salt resulting from this reaction is isolated and
   d) this salt is suspended in an inert solvent, and mixed with water until phase separation occurs and then adjusted to a pH in the range from 8 to 12, with a solution of a base, and the prolinol released from its salt is extracted and isolated.

2. The process as recited in claim 1 further characterized in that
   a) D- or L-proline is dissolved in dimethylformamide and reacted in the presence of an alkali metal salt with benzyl chloride at a temperature in the range from 60° to 100° C. and after cooling to a temperature in the range from 20° to 40° C., it is combined with water, the reaction mixture is extracted with toluene and the reaction product is then isolated and
   b) the protected D- or L-proline derivative is dissolved in tetrahydrofuran under an inert gas atmosphere and reacted with a phenyl magnesium or β-naphthyl magnesium halide at a temperature of 70° C. and, after the reaction mixture has cooled to a temperature in the range from 15° to 35° C. it is combined with dilute sulfuric acid, and adjusted to a pH of 7 and the aqueous phase is extracted with tetrahydrofuran and the dibenzylprolinol derivative is isolated and
   c) the dibenzylprolinol derivative is dissolved in ethanol and reacted in the presence of palladium on charcoal (10% ) with hydrogen under a pressure in the range from 3 to 7 bar, and the prolinol derivative, freed from the benzyl protecting group, after removal of the reaction medium, is dissolved in toluene, the solution is filtered and the filtrate is mixed with 15% sulfuric acid until a pH in the range from 2 to 3 is achieved, the salt resulting from this reaction is isolated and
   d) the salt is suspended in dichloromethane and water is added until phase separation occurs and the, pH is adjusted to 9 using 25% sodium hydroxide solution and the prolinol derivative liberated from its salt is extracted with dichloromethane and isolated.

3. The process as recited in claim 1 further characterized in that
   a) D- or L-proline is dissolved in an organic sulphoxide or acid amide and reacted with benzyl chloride in the presence of a compound if an alkali earth metal salt, at a range from 60° to 140° C. and, after cooling, combined with water, then the reaction mixture is extracted with a hydrocarbon and the dibenzyl protected D- or L-proline derivative isolated and
   b) the dibenzyl protected D- or L-proline derivative is dissolved in an ether under an inert gas atmosphere and reacted with an aryl Grignard compound at a temperature in the range from 50° to 90° C. and after the reaction mixture has cooled it is combined with a dilute solution of an inorganic acid, with cooling, and adjusted to a pH in the neutral range and the aqueous phase is extracted with an ether, and the dibenzylprolinol derivative is isolated and c) the dibenzyl prolinol derivative is dissolved in an alcohol and, in the presence of a substance with catalyses the reductive cleaving of the benzyl protecting group, it is reacted with hydrogen under elevated pressure in the range from 2 to 20 bar, and the prolinol derivative freed from the benzyl protecting group, after removal of the reaction medium, is dissolved in an aliphatic or aromatic hydrocarbon, the solution is filtered and the filtrate is combined with an aqueous solution of an inorganic acid, until a pH of less than 7 is achieved, the salt resulting from this reaction is isolated and d) this salt is suspended in a halogenated hydrocarbon, and mixed with water until phase separation occurs and then adjusted to a pH in the range from 8 to 12, with an aqueous solution of an alkali earth metal salt, and the prolinol released from its salt is extracted and isolated.

\* \* \* \* \*